United States Patent
Aamodt et al.

(10) Patent No.: US 6,325,969 B1
(45) Date of Patent: Dec. 4, 2001

(54) PAPER PRODUCT IMPREGNATED WITH CHEMICAL MATERIAL

(76) Inventors: James Aamodt, 4999 Pleasant Ridge Rd., The Dalles, OR (US) 97058; John Colvin, 1348 N. Locust, Canby, OR (US) 97013

(*) Notice: Subject to any disclaimer, the term of this patent is extended or adjusted under 35 U.S.C. 154(b) by 0 days.

(21) Appl. No.: 09/302,937

(22) Filed: Apr. 30, 1999

(51) Int. Cl.⁷ ............................................... A61L 9/00
(52) U.S. Cl. .................. 422/29; 422/28; 422/29; 422/37; 428/308.8; 428/311.11
(58) Field of Search ................................. 422/28, 29, 37; 424/413, 414, 415, 417; 428/514, 600, 308.8, 311.11

(56) References Cited

U.S. PATENT DOCUMENTS

| | | | |
|---|---|---|---|
| 2,883,322 | 4/1959 | Whipple | 167/39 |
| 3,293,114 | 12/1966 | Kenaga et al. | 162/168 |
| 4,115,422 | 9/1978 | Welch et al. | 260/429.3 |
| 4,119,577 | * 10/1978 | Light et al. | 252/522 |
| 4,172,841 | 10/1979 | Danna et al. | 260/429.9 |
| 4,174,418 | 11/1979 | Welch et al. | 428/264 |
| 4,199,322 | 4/1980 | Danna et al. | 8/186 |
| 4,259,383 | * 3/1981 | Eggensperger et al. | 422/29 |
| 4,401,712 | 8/1983 | Morrison . | |
| 4,430,381 | 2/1984 | Harvey et al. | 428/284 |
| 4,533,435 | 8/1985 | Intili . | |
| 4,541,944 | * 9/1985 | Sanderson | 252/95 |
| 4,597,940 | 7/1986 | Häger . | |
| 4,615,937 | 10/1986 | Bouchette . | |
| 4,692,374 | 9/1987 | Bouchette . | |
| 4,732,797 | 3/1988 | Johnson et al. | 428/74 |
| 4,737,405 | 4/1988 | Bouchette . | |
| 4,738,847 | 4/1988 | Rothe et al. | 424/443 |
| 4,740,398 | 4/1988 | Bouchette | 428/28 |
| 4,745,640 | 5/1988 | Nelson | 4/243 |
| 4,772,501 | 9/1988 | Johnson et al. | 428/74 |
| 4,808,466 | 2/1989 | Kotani et al. . | |
| 4,865,855 | 9/1989 | Hansen et al. . | |
| 4,900,765 | 2/1990 | Murabayashi et al. . | |
| 4,906,462 | 3/1990 | Miki et al. | 424/76.1 |
| 4,908,262 | 3/1990 | Nelson | 428/283 |
| 4,929,498 | 5/1990 | Suskind et al. . | |
| 4,983,441 | 1/1991 | Miki et al. | 428/65 |
| 5,049,440 | 9/1991 | Bornhoeft, III et al. | 428/288 |
| 5,066,686 | 11/1991 | Fodor et al. | 523/102 |
| 5,091,102 | 2/1992 | Sheridan . | |
| 5,104,660 | 4/1992 | Chvapil et al. | 424/445 |

(List continued on next page.)

FOREIGN PATENT DOCUMENTS

| | | |
|---|---|---|
| 0 423 817 A | 4/1991 | (EP) . |
| 2 759 911 A | 8/1998 | (FR) . |
| 98 11776 A | 3/1998 | (WO) . |

OTHER PUBLICATIONS

Holleman–Wiberg: Lehrbuch der Anorganischen Chemie, 91.–100. Auflage, Nils Wiberg; Walter de Gruyter 1985.

*Primary Examiner*—Robert J. Warden, Sr.
*Assistant Examiner*—Imad Soubra
(74) *Attorney, Agent, or Firm*—Mary R. Bonzagni, Esq.; Holland & Bonzagni, P.C

(57) ABSTRACT

The present invention provides a porous paper product impregnated with at least one chemical species. The porous paper product can be in the form of sheets, or compressed pellets. The porous paper can be prepared from a variety of sources, including wood pulp, kenaf, flax, or hemp. The chemical species impregnating the paper react and/or diffuse out of the paper to accomplish a variety of desired results. For example, diffusion of a volatile biocidal chemical out of pores in the paper create a no-growth zone on and immediately surrounding the impregnated paper. In this manner the impregnated paper can provide a sterile environment for activities such as food packaging/storage, the treatment of illness/injury, or waste disposal.

32 Claims, 1 Drawing Sheet

U.S. PATENT DOCUMENTS

| | | | |
|---|---|---|---|
| 5,116,620 | 5/1992 | Chvapil et al. | 424/445 |
| 5,141,803 | 8/1992 | Pregozen | 428/288 |
| 5,152,996 | 10/1992 | Corey et al. | 424/443 |
| 5,156,843 | 10/1992 | Leong et al. . | |
| 5,176,930 | 1/1993 | Kannankeril et al. . | |
| 5,227,168 | 7/1993 | Chvapil et al. | 421/445 |
| 5,278,112 | 1/1994 | Klatte | 502/62 |
| 5,296,239 | 3/1994 | Colery et al. | 424/613 |
| 5,314,852 | 5/1994 | Klatte | 502/60 |
| 5,427,844 | 6/1995 | Murai et al. | 428/245 |
| 5,464,598 | 11/1995 | Klatte | 423/220 |
| 5,567,405 | 10/1996 | Klatte et al. | 423/477 |
| 5,573,743 * | 11/1996 | Klatte et al. | 422/29 |
| 5,624,575 | 4/1997 | Meade et al. | 210/759 |
| 5,631,300 | 5/1997 | Wellinghoff . | |
| 5,656,037 | 8/1997 | Vigo et al. | 8/111 |
| 5,658,467 | 8/1997 | Lazonby et al. | 210/754 |
| 5,674,538 | 10/1997 | Lokkesmoe et al. | 424/616 |
| 5,700,742 | 12/1997 | Payne | 442/123 |
| 5,707,736 | 1/1998 | Levy et al. . | |
| 5,709,897 | 1/1998 | Pearlstein . | |
| 5,730,948 | 3/1998 | Klatte et al. | 423/477 |
| 5,776,850 | 7/1998 | Klatte et al. | 502/64 |
| 5,786,282 | 7/1998 | Carter et al. . | |
| 5,814,568 | 9/1998 | Kato et al. | 442/123 |
| 5,833,739 | 11/1998 | Klatte et al. | 95/136 |
| 5,845,769 | 12/1998 | Yeager . | |
| 5,853,689 | 12/1998 | Klatte | 423/478 |
| 5,869,172 | 2/1999 | Caldwell . | |
| 5,885,543 | 3/1999 | Klatte | 423/477 |
| 5,886,216 | 3/1999 | Pudas | 562/6 |
| 5,968,852 | 10/1999 | Vlasblom . | |
| 6,022,627 | 2/2000 | Weder . | |

* cited by examiner

PAPER PRODUCT IMPREGNATED WITH CHEMICAL MATERIAL

BACKGROUND OF THE INVENTION

1. Field of the Invention

The present invention relates to a paper product impregnated with chemical material to accomplish a variety of industrial and household tasks.

2. Description of the Related Art

Paper is typically formed from a mesh of fine fibers, generally of vegetable origin. Currently, wood pulp is the most common source for paper. However, other fibrous material such as cotton, flax, kenaf, hemp, or straw have been used in paper manufacture. Most commonly paper is produced in the form of thin sheets. However paper can also be manufactured in other physical forms such as compressed pellets.

Paper products currently enjoy widespread use in almost every field of human endeavor. Paper is used as sterile packaging for surgical instruments, and as a cheap, disposable covering for surfaces in treatment and operating rooms. In the food service industry, paper is universally utilized to store both solid and liquid foods, as well as to serve those foods to the consumer. Paper is also emerging as a major component in absorbent material for disposal of wastes from pets and other sources, for example in the material known as cat litter.

Given the wide uses for paper products, there is a need in the art for a paper product which receives, retains, and releases useful chemical species.

Unfortunately, paper provides a suitable environment for the growth of microorganisms. The ability of paper to support the growth of bacteria, molds, or fungi is attributable to the fact that paper is itself is derived from living tissue and contains residual organic material that can provide sustenance for microorganisms.

The unwanted growth of microorganisms poses a health hazard for many of the potential applications for paper products For example, maintaining a sterile environment during the treatment of illness and injury has proven to dramatically reduce the possibility of infection. In the area of food services, maintaining an micro-organism free environment prolongs the viability of foodstuffs, and enhances the effect of such processes as pasteurization. In waste disposal applications, reduction in the growth of microorganisms can cut down on noxious odors and the danger of infection to waste-handlers.

Therefore, there is also a need in the art for a paper product which can inhibit the growth of microorganisms, and which is cheap and easy to manufacture.

SUMMARY OF THE INVENTION

The present invention relates to a porous paper material which has been impregnated with at least one chemical material. The impregnating chemical may beneficially react with other chemicals.

In one embodiment, paper is impregnated with hydrogen peroxide and acetic acid, and reaction between the hydrogen peroxide and acetic acid creates peracetic acid. Peracetic acid is both biocidal and volatile. The gaseous peracetic acid diffuses out of pores in the paper, creating a no-growth zone on the surface of and immediately surrounding the paper. In this manner, chemically impregnated paper in accordance with the present invention may promote a sterile environment useful for a wide variety of activities, for example in the treatment of illness/injury, or in the packaging/storage of foodstuffs.

A method for sterilizing an area in accordance with the present invention comprises the steps of impregnating a porous paper product with a chemical material, placing the porous paper product in the area, and causing reaction of the impregnated chemical material to produce a biocidal compound.

A method for impregnating a porous paper product in accordance with one embodiment of the present invention comprises the steps of providing the porous paper product having pores and a surface, and exposing the surface of the porous paper product to at least one chemical which conveys biocidal properties to the porous paper product.

A composition for producing peracetic acid in accordance with one embodiment of the present invention comprises a porous paper product impregnated with hydrogen peroxide and an acid.

The features and advantages of the present invention will be understood upon consideration of the following detailed description of the invention and the accompanying drawings.

DETAILED DESCRIPTION

Figure 1:
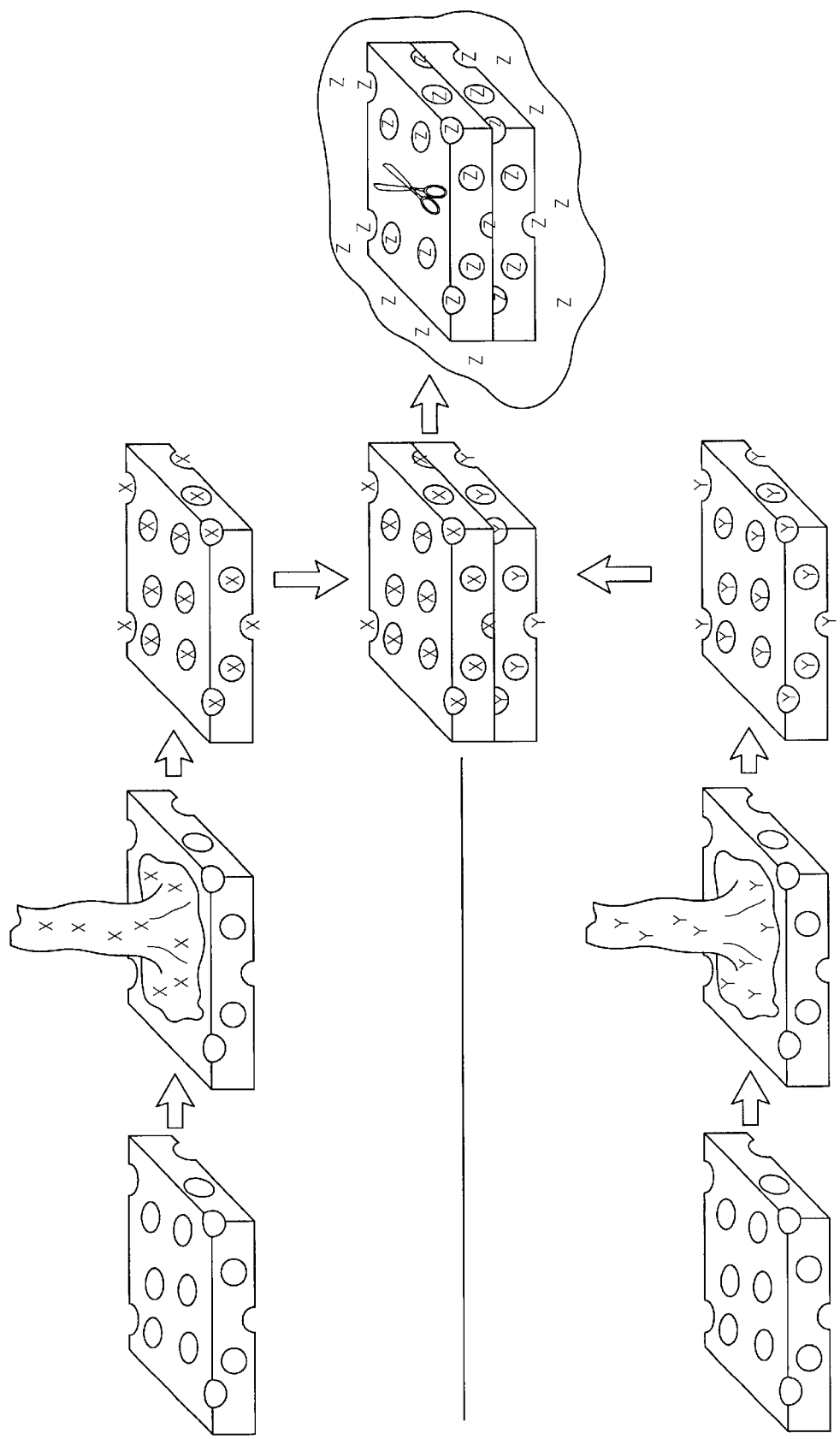
FIG. 1 illustrates a method for creating a sterile field utilizing chemically impregnated sheets of paper in accordance with one embodiment of the present invention.

The present invention relates to a paper product that has been impregnated with at least one chemical. Reaction and/or diffusion of this chemical out of the pores of the paper gives rise to a number of beneficial properties. In particular, diffusion of an impregnating volatile antimicrobial or biocidal agent creates a sterile environment at the surface and in the immediate vicinity of the paper.

Paper is a highly porous material. These pores are defined by space between the extremely fine vegetable fibers making up the mesh. The pores in the paper can receive and contain a wide variety of chemical materials.

For example, the pores in paper can be impregnated with precursors of chlorine dioxide ($ClO_2$), a gas useful for killing biological contaminants (such as microorganisms, mold, fungi, yeast and bacteria). The biocidal nature of $ClO_2$ is attributable to its high oxidation potential.

Chlorine dioxide can be produced in many ways. For example, it is known to generate chlorine dioxide by adding an acid to a metal chlorite solution. Chlorine dioxide can also be generated by adding water to a powdered composition such as ferric sulfate or ferric chloride (or other dry composition). An activated dry composition which absorbs water from the air and releases chlorine dioxide over time may also be prepared.

In a first class of embodiments of the present invention, a sheet of paper is successively impregnated with sodium chlorite and acetic acid, or one sheet of paper impregnated with sodium chlorite is placed into contact with another sheet of paper impregnated with acetic acid. Mixing by co-diffusion of the two chemicals causes in the following reaction:

| $CH_3COOH$ + | $NaClO_2$ - - > | $ClO_2$ |
|---|---|---|
| acetic | sodium | chlorine |
| acid | chlorite | dioxide |

The volatile chlorine dioxide then diffuses from pores of the paper into the surrounding environment. The chlorine dioxide suppresses growth of bacteria, molds, or fungi on the surface of the paper or in areas immediately surrounding the paper.

Acetic acid is only one acid that can generate chlorine dioxide in accordance with the present invention. Sulfuric acid, phosphoric acid, and propionic acid can also react with sodium chlorite to produce chlorine dioxide. Moreover, these acids can also react with paper impregnated with sodium chlorate to produce chlorine dioxide.

FIG. 1 illustrates one embodiment of the present invention, wherein separate sheets of paper 10A and 10B are impregnated with sodium chlorite X and acetic acid Y, respectively. Impregnated papers 10A and 10B are separately stored and transported to the site of use, such as a hospital operating room. At the point of use, impregnated papers 10A and 10B are placed in physical contact. Co-diffusion of the sodium chlorite X and acetic acid Y promotes reaction between these chemicals, forming volatile chlorine dioxide Z. Chlorine dioxide Z outgasses from combined papers 10C, inhibiting the growth of microorganisms on the surface of the combined papers 10C as well as in immediate vicinity 10D of combined papers 10C. This outgassing provides a sterile environment for surgical instrument 12.

In another embodiment of the present invention, a porous paper product in the form of pellets is impregnated with sodium chlorite and acetic acid. Alternatively, a first bed of paper pellets is impregnated with sodium chlorite, and a second bed of paper pellets is impregnated with acetic acid. Mixing together of pellets from the two beds can promote the formation of chlorine dioxide.

In a further alternative embodiment of the present invention, a porous paper product in the form of sheets or pellets is successively impregnated with hydrogen peroxide and an acid. Mixing by co-diffusion of the two impregnating compounds produces a peracid. Acids which may be mixed with hydrogen peroxide to produce the corresponding peracid include but are not limited to: acetic acid; propionic acid; citric acid; benezoic acid; phosphoric acid; lactic acid; butyric acid; pentenoic acid; succinic acid; glutaric acid; sorbic acid; and glycolic acid.

The following chemical reaction shows the specific reaction between acetic acid and hydrogen peroxide to produce peracetic acid:

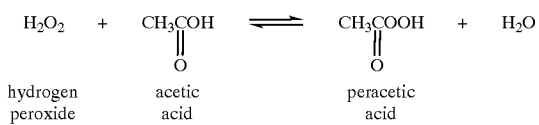

$$H_2O_2 \quad + \quad CH_3\overset{\underset{\|}{O}}{C}OH \quad \rightleftharpoons \quad CH_3\overset{\underset{\|}{O}}{C}OOH \quad + \quad H_2O$$

hydrogen peroxide    acetic acid    peracetic acid

Like chlorine dioxide, peracetic acid is a volatile gas having a high oxidation potential and corresponding biocidal properties. Diffusing peracetic acid creates the same type of sterile field discussed above in connection with chlorine dioxide.

A variety of methods may be utilized to impregnate the paper with chemical materials. For example, the paper may be dunked or immersed in a bath containing the chemical, with the liquid chemical drawn into the pores of the paper through the process of diffusion. Alternatively, the chemical may be sprayed upon the surface of the paper, with impregnation of the paper accomplished through diffusion of the chemical from the paper's surface into the underlying pores.

The present invention is applicable to impregnate a variety of porous paper products. Paper made from softwood pulp, kenaf, flax, and hemp are all suitable for chemical impregnation in accordance with the present invention.

In order to further illustrate the present invention, the following experimental examples are described. Each of these examples illustrates impregnation of paper with chemicals that impart biocidal properties

EXAMPLE NUMBER 1

The antimicrobial properties of a number of samples of impregnated kenaf papers was determined by exposing *E. coli* bacteria during its growth period to the impregnated paper. This was done by using a zone of inhibition test.

A half inch square of the impregnated sample kenaf paper was placed in the center of a Petri dish containing an agar and *E. coli* bacteria spread on the agar surface. Where *E. coli* bacteria were unable to multiply to form visible colonies due to the effects of the test paper, the agar media remained clear. This clear area is known as the zone of inhibition. Bacteria outside of this zone of inhibition are not affected by their proximity to the sample and grow to form visible colonies.

A number of samples were prepared according to TABLE 1:

TABLE 1

| Sample Number | Sample Components (all % by weight) |
|---|---|
| 1 | 35% aqueous hydrogen peroxide 99% acetic acid |
| 2 | paper only - no impregnated chemicals |
| 3 | 5% limonene in water |
| 4 | 5% limonene in water 35% aqueous hydrogen peroxide |
| 5 | 50% aqueous potassium sorbate 99% acetic acid |
| 6 | 50% aqueous potassium sorbate 5% limonene in water |
| 7 | 50% aqueous potassium sorbate 35% aqueous hydrogen peroxide |

The chemicals to be impregnated in each sample were sprayed onto sheets of kenaf paper in equal parts of 2 cc/ft² of paper surface area. The paper was allowed to dry, and a ½"×½" square of the impregnated paper was cut to serve as a sample.

A petri dish with Standard Plate Count Agar was inoculated with *E. coli* bacteria by using a bottle with 99 ml sterile phosphate-buffered dilution water, to which is added one loopful of diluted *E. coli* culture. A sterile cotton swab was dipped into the dilution water containing the *E. coli* culture, then the swab was liberally wiped over the entire surface of the agar. After this, the ½ inch square of the paper sample was placed in the middle of the dish, and the dish was then sealed. After two days growth at 35° C., the zone of inhibition around the paper was measured from all four sides and averaged.

The results of the zone of inhibition test for *E. coli* bacteria for the samples listed in TABLE 1 are shown in TABLE 2:

TABLE 2

Zone of Inhibition Test Using *E. Coli* Bacteria

| Sample # | Side #1 | Side #2 | Side #3 | Side #4 | Avg. Length |
|---|---|---|---|---|---|
| 1 | 2.6 cm | 2.7 cm | 2.6 cm | 2.6 cm | 2.63 cm |
| 2 | 0.0 cm | 0.0 cm | 0.0 cm | 0.0 cm | 0.0 cm |
| 3 | 0.0 cm | 0.0 cm | 0.0 cm | 0.0 cm | 0.0 cm |
| 4 | 2.9 cm | 2.8 cm | 3.0 cm | 2.7 cm | 2.85 cm |
| 5 | 1.3 cm | 1.0 cm | 1.0 cm | 1.1 cm | 1.1 cm |

TABLE 2-continued

Zone of Inhibition Test Using *E. Coli* Bacteria

| Sample # | Side #1 | Side #2 | Side #3 | Side #4 | Avg. Length |
|---|---|---|---|---|---|
| 6 | 1.0 cm | 1.1 cm | 1.0 cm | 1.0 cm | 1.03 cm |
| 7 | 0.5 cm | 0.6 cm | 0.5 cm | 0.5 cm | 0.53 cm |

Review of TABLE 2 indicates that sample no. 4 (5% limonene/35% aqueous hydrogen peroxide) was most effective in inhibiting the growth of the *E. coli* bacteria. Sample no. 1 (99% acetic acid/35% aqueous hydrogen peroxide) was the next most effective mixture. Neither the control (sample no. 2) nor limonene alone (sample no. 3) showed any effectiveness against the *E. coli* bacteria.

EXAMPLE NUMBER 2

A second zone of inhibition test was next performed to test the ability of the samples of TABLE 1 to inhibit growth of the Penicillium mold.

A Petri dish with Standard Plate Count Agar was inoculated with a wild strain of the Penicillium mold by using a bottle with 99 ml sterile phosphate-buffered dilution water, to which was added a moistened cotton swab that has been rubbed on the top of a growing colony of Penicillium. A new sterile cotton swab was dipped into the dilution water containing the Penicillium culture, then the swab was liberally wiped over the entire surface of the agar. After this, a ½ inch square of the paper sample was placed in the middle of the dish, and the dish was then sealed.

After four days growth at room temperature, the zone of inhibition was measured from all four sides and averaged. The results are shown in TABLE 3:

TABLE 3

Zone of Inhibition Test Using Wild Strain of Penicillium Mold

| Sample # | Side #1 | Side #2 | Side #3 | Side #4 | Avg. Length |
|---|---|---|---|---|---|
| 1 | 1.8 cm | 1.7 cm | 1.8 cm | 1.9 cm | 1.8 cm |
| 2 | 0.0 cm | 0.0 cm | 0.0 cm | 0.0 cm | 0.0 cm |
| 3 | 0.0 cm | 0.0 cm | 0.0 cm | 0.0 cm | 0.0 cm |
| 4 | 2.3 cm | 2.2 cm | 2.3 cm | 2.2 cm | 2.25 cm |
| 5 | 1.1 cm | 1.0 cm | 1.0 cm | 1.0 cm | 1.02 cm |
| 6 | 0.0 cm | 0.0 cm | 0.0 cm | 0.0 cm | 0.0 cm |
| 7 | 0.0 cm | 0.0 cm | 0.0 cm | 0.0 cm | 0.0 cm |

Review of TABLE 3 indicates that sample no. 4 (5% limonene/35% aqueous hydrogen peroxide) was again most effective at inhibiting the growth of microorganisms. Sample no. 1 (99% acetic acid/35% aqueous hydrogen peroxide) was again the next most effective mixture. Neither the control (sample no. 2) limonene alone (sample no. 3) showed any effectiveness against the Penicillium mold.

EXAMPLE NUMBER 3

To evaluate the effect upon biocidal activity of the type of paper impregnated with chemical species, a third zone of inhibition test was conducted. This test utilized a second set of samples prepared according to TABLE 4:

TABLE 4

| Sample Number | Paper Type | Sample Components (all % by weight) |
|---|---|---|
| 8 | flax | 50% aqueous citric acid |
|   |   | 35% aqueous hydrogen peroxide |
| 9 | hemp | 50% aqueous citric acid |
|   |   | 35% aqueous hydrogen peroxide |
| 10 | kenaf | 50% aqueous citric acid |
|   |   | 35% aqueous hydrogen peroxide |
| 11 | wood pulp | 50% aqueous citric acid |
|   |   | 35% aqueous hydrogen peroxide |
| 12 | kenaf | 100% 50% aqueous citric acid |
| 13 | kenaf | 100% 35% aqueous hydrogen peroxide |

Again, the components of each sample were sprayed onto the paper in equal parts of 2 cc/ft$^2$ of paper surface area. The paper was allowed to dry, and a ½"×½" square of the impregnated paper were then cut to serve as a sample.

A zone of inhibition test was then performed in the presence of *E. coli* bacteria, as otherwise described above in Example Number 1. The results are shown in TABLE 5:

TABLE 5

Zone of Inhibition Test Using *E. Coli* Bacteria

| Sample # | Side #1 | Side #2 | Side #3 | Side #4 | Avg. Length |
|---|---|---|---|---|---|
| 8 | 1.6 cm | 1.4 cm | 2.0 cm | 2.4 cm | 1.85 cm |
| 9 | 1.1 cm | 1.6 cm | 1.8 cm | 1.3 cm | 1.45 cm |
| 10 | 1.9 cm | 2.4 cm | 2.6 cm | 2.7 cm | 2.40 cm |
| 11 | >3.3 cm | 3.0 cm | 2.8 cm | 2.9 cm | >3.00 cm |
| 12 | 1.6 cm | 1.5 cm | 1.4 cm | 1.5 cm | 1.50 cm |
| 13 | 2.4 cm | 2.9 cm | 2.8 cm | 2.8 cm | 2.73 cm |

Review of TABLE 5 indicates that sample no. 11 (50% citric acid/35% aqueous hydrogen peroxide in wood pulp paper) was the most effective at inhibiting the growth of the *E. coli* bacteria. Sample no. 13 (35% aqueous hydrogen peroxide in kenaf paper) was the next most effective mixture. Hemp paper impregnated with the citric acid/hydrogen peroxide combination evidenced the least biocide activity.

EXAMPLE NUMBER 4

A zone of inhibition test of the samples of TABLE 4 in the presence of the Penicillium mold. The experiment was otherwise conducted in the general manner described above in connection with Example Number 2. The results are shown below in TABLE 6:

TABLE 6

Zone of Inhibition Test Using Wild Strain of Penicillium Mold

| Sample # | Side #1 | Side #2 | Side #3 | Side #4 | Avg. Length |
|---|---|---|---|---|---|
| 8 | 1.9 cm | 2.0 cm | 2.0 cm | 1.8 cm | 1.92 cm |
| 9 | 2.3 cm | 2.0 cm | 2.1 cm | 1.9 cm | 2.07 cm |
| 10 | 2.9 cm | 2.7 cm | 2.8 cm | 2.9 cm | 2.82 cm |
| 11 | 2.6 cm | 2.3 cm | 2.2 cm | 2.4 cm | 2.37 cm |
| 12 | 0.0 cm | 0.0 cm | 0.0 cm | 0.0 cm | 0.0 cm |
| 13 | 1.9 cm | 2.0 cm | 2.1 cm | 1.9 cm | 1.97 cm |

Review of TABLE 6 indicates that sample no. 9 (50% citric acid/35% aqueous hydrogen peroxide in kenaf paper) was the most effective at inhibiting the growth of the Penicillium mold. Sample no. 11 (50% citric acid/35% aqueous hydrogen peroxide in wood paper) was the next most effective combination. Kenaf paper impregnated with citric acid exhibited no biocidal activity.

The impregnated paper product in accordance with the present invention offers a number of important advantages. One advantage is that the paper can be impregnated with the chemical species directly during the paper-making process. For example, before a large sheet of paper is spooled during manufacture, it can be sprayed with a chemical or immersed in a chemical bath. Similarly, paper pellets can be sprayed or immersed in the chemical immediately after assuming their final physical form.

Yet another advantage of chemically-impregnated paper in accordance with the present invention is that its relatively cheap cost facilitates replacement when the impregnating chemical material becomes spent or exhausted. This is particularly important in medical treatment applications having a low tolerance for contamination, which require frequent replacement of materials in order to maintain the integrity of the sterile field.

Another important advantage of the present invention is its environmental compatibility Examples 1–4 reveal that impregnated kenaf paper has significant biocidal capability. Kenaf is an annual plant having a paper producing potential approximating that of wood, making it an environmentally-friendly alternative paper source. Moreover, the impregnating chemicals acetic acid, citric acid, and limonene are both readily obtained from natural sources. Acetic acid can be obtained by fermentation, citric acid is present in fruits, and limonene is derived from orange peels.

Although the invention has been described in connection with specific embodiments, it must be understood that the invention as claimed should not be unduly limited to these embodiments. Various other modifications and alterations in the structure and process will be apparent to those skilled in the art without departing from the scope of the present invention.

For example, while the embodiment of the present invention shown in FIG. 1 describes generating chlorine dioxide from the combination of sodium chlorite and acetic acid, the invention is not limited to these impregnated chemicals. The combination of sodium chlorate and sulfuric acid would also function to generate chlorine dioxide. This is also true for the combination of either sodium chlorate or sodium chlorite and either ferric chlorate or ferric sulfate.

Moreover, while experimental results have been reported above in conjunction with impregnation of paper with chemicals imparting biocidal activity, paper could be impregnated with a wide variety of other types of chemicals in accordance with the present invention. TABLE 7 provides a partial listing of possible chemicals and chemical combinations suitable for impregnating paper in accordance with the present invention:

TABLE 7

| IMPREGNATING CHEMICAL SPECIES | PRODUCT CHEMICAL SPECIES | USES FOR PRODUCT CHEMICAL SPECIES |
|---|---|---|
| 1) hydrogen peroxide 2) acid (ex. acetic acid) | peracid | biocide |
| 1) sodium chlorite/ sodium chlorate 2) acid (ex. acetic acid)/or | chlorine dioxide | biocide |

TABLE 7-continued

| IMPREGNATING CHEMICAL SPECIES | PRODUCT CHEMICAL SPECIES | USES FOR PRODUCT CHEMICAL SPECIES |
|---|---|---|
| metal salt (ex. ferric sulfate) phosphoric acid | $(NH_4)_2HPO_4$ | odor control (absorption of ammonia) |
| 1) permanganate (ex. potassium permanganate) 2) quarternary ammonium cation (ex. cetyltrimethylammonium) | $CO_2 + H_2O$ | oxidation and removal of organic contaminants from a mixture |
| potassium hydroxide | $KClO_2 + KClO_4$ | removal of $ClO_2$ |
| sodium sulfite/or sodium bisulfite | $S_2O_5 + H^+_3ClO_3$ | removal of $ClO_2$ |
| manganese dioxide | — | molecular sieve (filtration) |

Examples of the chemicals (or inhibitors of chemicals) usefully impregnated into porous paper products (e.g. sheets of paper or paper pellets) include the following: sodium chlorate; sodium chlorite; ferric chloride; ferric sulfate; peracetic acid; percitric acid; phosphoric acid; sulfuric acid; propionic acid; citric acid; acetic acid; hydrogen peroxide; calcium chloride; magnesium sulfate; potassium chloride; magnesium chloride; sodium bisulfite; sodium metabisulfite; sodium sulfite; limonene; potassium sorbate; potassium hydroxide; amino acids; quarternary ammonium cation (including but not limited to cetyltrimethylammonium chloride); urea; free amines; copper sulfate; zinc sulfate; cobalt sulfate; magnesium sulfate; copper chloride; zinc chloride; cobalt chloride; magnesium chloride; manganese sulfate; manganese chloride; manganese dioxide; sodium selenate; permanganates (including but not limited to potassium permanganate); chlorine; vitamins; lactic acid; benzoic acid; butyric acid; pentenoic acid; succinic acid; glutaric acid; and glycolic acid.

Given the multitude of embodiments described above, it is therefore intended that the following claims define the scope of the present invention, and that the compositions and methods within the scope of these claims and their equivalents be covered hereby.

What is claimed is:

1. A method for sterilizing an area comprising:

impregnating a first paper product with a first chemical material, wherein the first chemical material is capable of reacting with a second chemical material to produce an antimicrobial or biocidal chemical material, impregnating a second paper product with the second chemical material, reacting the first and the second chemical materials by physically contacting the impregnated first and second paper products and the first and the second chemical materials, and placing the impregnated first and second paper products in the area to be sterilized, wherein, the first chemical material is selected from a metal chlorite and hydrogen peroxide, wherein, the second chemical material is selected from an acid and a metal salt, and wherein, the antimicrobial or biocidal chemical material is selected from a peracid and chlorine dioxide.

2. The method of claim 1, wherein the first chemical material is an antimicrobial or biocidal chemical material which comprises a combination of an alkali metal sorbate and an acid, wherein the acid is selected from acetic acid, ascorbic acid, benzoic acid, butyric acid, citric acid, glutaric acid, glycolic acid, lactic acid, pentanoic acid, phosphoric acid, proprionic acid, and succinic acid.

3. The method of claim 2, wherein the first chemical material is an antimicrobial chemical material which comprises a combination of an alkali metal sorbate and citric acid.

4. The method of claim 3, wherein the alkali metal sorbate is potassium sorbate.

5. The method of claim 1, wherein the first paper product is in the form of a paper sheet.

6. The method of claim 1, wherein the second paper product is in the form of a paper sheet.

7. The method of claim 1, wherein the first chemical material is an antimicrobial chemical material which comprises an alkali metal sorbate.

8. The method of claim 7, wherein the alkali metal sorbate is potassium sorbate.

9. The method of claim 1, wherein the first chemical material is a biocidal chemical material which comprises hydrogen peroxide.

10. The method of claim 1, wherein the first chemical material is a biocidal chemical material which comprises d-limonene.

11. The method of claim 1, wherein the first chemical material is a biocidal chemical material which comprises phosphoric acid.

12. The method of claim 1, wherein the first chemical material is capable of reacting with a second chemical material to produce a peracid.

13. The method of claim 12, wherein the first chemical material is hydrogen peroxide, and wherein the second chemical material is an acid selected from acetic acid, ascorbic acid, butyric acid, citric acid, glycolic acid, and lactic acid.

14. The method of claim 1, wherein the first chemical material is capable of reacting with a second chemical material to produce chlorine dioxide.

15. The method of claim 14, wherein the first chemical material is a metal chlorite, and wherein the second chemical material is an acid selected from acetic acid, ascorbic acid, benzoic acid, butyric acid, citric acid, glutaric acid, glycolic acid, lactic acid, pentanoic acid, phosphoric acid, proprionic acid, and succinic acid.

16. The method of claim 14, wherein the first chemical material is a metal chlorite, and wherein the second chemical material is a metal salt.

17. A paper product for use in sterilizing an area, which comprises:
  a first paper component impregnated with a first chemical material, wherein the first chemical material is capable of reacting with a second chemical material to produce an antimicrobial or biocidal chemical material,
  a second paper component impregnated with the second chemical material,
  wherein, the first and second chemical materials react when the first paper component physically contacts the second paper component and when the first chemical material physically contacts the second chemical material,
  wherein, the first chemical material is selected from a metal chlorite and hydrogen peroxide,
  wherein, the second chemical material is selected from an acid and a metal salt, and
  wherein, the antimicrobial or biocidal chemical material is selected from a peracid and chlorine dioxide.

18. The paper product of claim 17, wherein the first chemical material is an antimicrobial or biocidal chemical material which comprises a combination of an alkali metal sorbate and an acid, wherein the acid is selected from acetic acid, ascorbic acid, benzoic acid, butyric acid, citric acid, glutaric acid, glycolic acid, lactic acid, pentanoic acid, phosphoric acid, proprionic acid, and succinic acid.

19. The paper product of claim 18, wherein the first chemical material is an antimicrobial chemical material which comprises a combination of an alkali metal sorbate and citric acid.

20. The paper product of claim 19, wherein the alkali metal sorbate is potassium sorbate.

21. The paper product of claim 17, wherein the first paper component is in the form of a paper sheet.

22. The paper product of claim 17, wherein the second paper component is in the form of a paper sheet.

23. The paper product of claim 17, wherein the first chemical material is an antimicrobial chemical material which comprises an alkali metal sorbate.

24. The paper product of claim 23, wherein the alkali metal sorbate is potassium sorbate.

25. The paper product of claim 17, wherein the first chemical material is a biocidal chemical material which comprises hydrogen peroxide.

26. The paper product of claim 17, wherein the first chemical material is a biocidal chemical material which comprises d-limonene.

27. The paper product of claim 17, wherein the first chemical material is a biocidal chemical material which comprises phosphoric acid.

28. The paper product of claim 17, wherein the first chemical material is capable of reacting with a second chemical material to produce a peracid.

29. The paper product of claim 28, wherein the first chemical material is hydrogen peroxide, and wherein the second chemical material is an acid selected from acetic acid, ascorbic acid, butyric acid, citric acid, glycolic acid, and lactic acid.

30. The paper product of claim 17, wherein the first chemical material is capable of reacting with a second chemical material to produce chlorine dioxide.

31. The paper product of claim 30, wherein the first chemical material is a metal chlorite, and wherein the second chemical material is an acid selected from acetic acid, ascorbic acid, benzoic acid, butyric acid, citric acid, glutaric acid, glycolic acid, lactic acid, pentanoic acid, phosphoric acid, proprionic acid, and succinic acid.

32. The paper product of claim 31, wherein the first chemical material is a metal chlorite, and wherein the second chemical material is a metal salt.

* * * * *

UNITED STATES PATENT AND TRADEMARK OFFICE
CERTIFICATE OF CORRECTION

PATENT NO.   : 6,325,969 B1                                              Page 1 of 2
DATED        : December 4, 2001
INVENTOR(S)  : Aamodt et al.

It is certified that error appears in the above-identified patent and that said Letters Patent is hereby corrected as shown below:

Columns 8-10,
Delete Claims 2 to 4, 7 to 11, 18 to 20 and 23 to 27.

Columns 9 and 10,
Renumber remaining Claims 5, 6, 12 to 17, 21, 22 and 28 to 32 as follows:
Claim 5 shall be renumbered Claim 2
Claim 6 shall be renumbered Claim 3
Claim 12 shall be renumbered Claim 4
Claim 13 shall be renumbered Claim 5
Claim 14 shall be renumbered Claim 6
Claim 15 shall be renumbered Claim 7
Claim 16 shall be renumbered Claim 8
Claim 17 shall be renumbered Claim 9
Claim 21 shall be renumbered Claim 10
Claim 22 shall be renumbered Claim 11
Claim 28 shall be renumbered Claim 12
Claim 29 shall be renumbered Claim 13
Claim 30 shall be renumbered Claim 14
Claim 31 shall be renumbered Claim 15
Claim 32 shall be renumbered Claim 16

Column 9,
Amend remaining claims as follows:
Line 32, delete "claim 12" and replace with -- claim 4 --
Lines 40 and 46, delete "claim 14" and replace with -- claim 6 --

UNITED STATES PATENT AND TRADEMARK OFFICE
CERTIFICATE OF CORRECTION

PATENT NO.  : 6,325,969 B1
DATED       : December 4, 2001
INVENTOR(S) : Aamodt et al.

It is certified that error appears in the above-identified patent and that said Letters Patent is hereby corrected as shown below:

<u>Column 10,</u>
Amend remaining claims as follows:
Lines 20, 22, 39 and 47, delete "claim 17" and replace with -- claim 9 --
Line 42, delete "claim 28" and replace with -- claim 12 --
Line 50, delete "claim 30" and replace with -- claim 14 --
Line 56, delete "claim 31" and replace with -- claim 14 --

Signed and Sealed this

Fourteenth Day of May, 2002

*Attest:*

JAMES E. ROGAN
*Attesting Officer*   *Director of the United States Patent and Trademark Office*